US008292824B2

(12) United States Patent
Okada

(10) Patent No.: US 8,292,824 B2
(45) Date of Patent: Oct. 23, 2012

(54) BIOPSY DEVICE

(75) Inventor: Naoyuki Okada, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 24 days.

(21) Appl. No.: 12/588,933

(22) Filed: Nov. 3, 2009

(65) Prior Publication Data

US 2010/0113970 A1    May 6, 2010

(30) Foreign Application Priority Data

Nov. 5, 2008   (JP) ................................. 2008-284382

(51) Int. Cl.
*A61B 5/00* (2006.01)

(52) U.S. Cl. ........................................................ 600/564

(58) Field of Classification Search .................. 600/562, 600/565, 566, 567
See application file for complete search history.

(56) References Cited

U.S. PATENT DOCUMENTS

| 4,798,212 A * | 1/1989 | Arana ............................ 600/562 |
| 5,219,351 A * | 6/1993 | Teubner et al. ................ 606/130 |
| 5,499,989 A * | 3/1996 | LaBash ........................... 606/130 |
| 5,712,890 A * | 1/1998 | Spivey et al. ..................... 378/37 |
| 5,964,715 A * | 10/1999 | Thunberg ....................... 600/562 |
| 6,334,067 B1 * | 12/2001 | Brabrand ........................ 600/427 |
| 2005/0203413 A1 * | 9/2005 | Fichtinger et al. ............. 600/461 |
| 2006/0173480 A1 * | 8/2006 | Zhang ............................ 606/185 |

FOREIGN PATENT DOCUMENTS

| JP | 10-165403 | 6/1998 |
| JP | 10-201749 | 8/1998 |

* cited by examiner

*Primary Examiner* — Max Hindenburg
(74) *Attorney, Agent, or Firm* — Jean C. Edwards; Edwards Neils PLLC

(57) ABSTRACT

A biopsy device includes a support base for supporting a mass to be examined, a compression plate for compressing and holding the mass to be examined against the support base, and a biopsy needle moving mechanism for moving a biopsy needle in a plane along the compression plate as well as in directions perpendicular to the compression plate. The biopsy needle is movable through an opening defined in the compression plate for insertion into the mass to be examined. The biopsy device also includes a determining section for determining whether or not the biopsy needle has pierced the mass to be examined, and a movement limiter for limiting movement of the biopsy needle within a plane perpendicular to a piercing direction along which the biopsy needle pierces the mass to be examined, if the determining section judges that the biopsy needle has pierced the mass to be examined.

9 Claims, 7 Drawing Sheets

BIOPSY DEVICE

CROSS-REFERENCE TO RELATED APPLICATION

This application is based upon and claims the benefit of priority from Patent Application No. 2008-284382 filed on Nov. 5, 2008, in the Japan Patent Office, of which the contents are incorporated herein by reference.

BACKGROUND OF THE INVENTION

1. Field of the Invention

The present invention relates to a biopsy device for removing a tissue sample from a mass to be examined through a biopsy needle, which is inserted into the mass to be examined.

2. Description of the Related Art

Biopsy devices have been developed for removing a tissue sample from a suspicious region of a subject, and for examining the tissue sample in order to perform a disease diagnosis on a patient.

Japanese Laid-Open Patent Publication No. 10-201749 discloses a system, which includes a mammographic apparatus for acquiring radiographic images of the breast region of a patient to be examined, together with a biopsy device that is incorporated into the mammographic apparatus. According to the disclosed system, the breast is positioned between an image capturing base and a compression plate, and then the breast is imaged from two directions in order to produce stereographic image information. Based on the stereographic image information, the positional information of a region to be biopsied is obtained. Then, the biopsy device, which is incorporated into the mammographic apparatus, is operated so as to insert a biopsy needle into the region to be biopsied according to the acquired positional information, whereby a tissue from the region to be biopsied is sampled.

Japanese Laid-Open Patent Publication No. 10-165403 discloses a biopsy device in detail. As shown in FIG. 7 of the accompanying drawings, the biopsy device includes a compression plate 4, which compresses and positions the breast 6 against a support base 2, and a biopsy needle 10, which is inserted into the breast 6 that has been positioned through an opening 8 defined in the compression plate 4. A tissue sample then is removed from the breast 6 through the biopsy needle 10. The biopsy needle 10 is held by a robot arm assembly 12, which is movably mounted on the compression plate 4. The robot arm assembly 12 includes a first arm 16 having an end pivotally supported on a post 14 fixed to the compression plate 4, and which is angularly movable about the post 14 in the directions indicated by the arrows parallel to the compression plate 4, and a second arm 18 having an end pivotally supported on the other end of the first arm 16, and which is angularly movable about the other end of the first arm 16 in the directions indicated by the arrows parallel to the compression plate 4. The biopsy needle 10 is mounted on the other end of the second arm 18 for movement in the directions indicated by the arrows, which are perpendicular to the compression plate 4. Based on the positional information of the desired region of the breast 6 to be biopsied, which has been acquired by a modality such as an MRI system or the like, the robot arm assembly 12 is controlled in motion so as to bring the biopsy needle 10 toward the region to be biopsied in order to remove a tissue sample therefrom.

If the robot arm assembly 12 is moved accidentally while the biopsy needle 10 resides within the breast 6, then the breast tissue may possibly become damaged by the biopsy needle 10. The robot arm assembly 12 could accidentally be moved when a technician operates the biopsy device by mistake, or if the robot arm assembly 12 moves in error.

SUMMARY OF THE INVENTION

It is an object of the present invention to provide a biopsy device, which includes a means for preventing the tissue of a subject to be biopsied from being unduly damaged by mistaken operations or by erroneous movements.

A biopsy device according to the present invention includes a biopsy needle moving mechanism for moving a biopsy needle to be inserted into a biopsy region of a mass to be examined, a determining section for determining whether the biopsy needle has pierced the mass to be examined or not, and a movement limiter for limiting movement of the biopsy needle within a plane perpendicular to a piercing direction along which the biopsy needle pierces the mass to be examined, if the determining section judges that the biopsy needle has pierced the mass to be examined.

When the determining section judges that the biopsy needle has pierced the mass to be examined, the movement limiter limits movement of the biopsy needle. Therefore, the tissue of the mass to be examined is reliably prevented from becoming accidentally damaged while the biopsy needle is being inserted into the mass to be examined.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
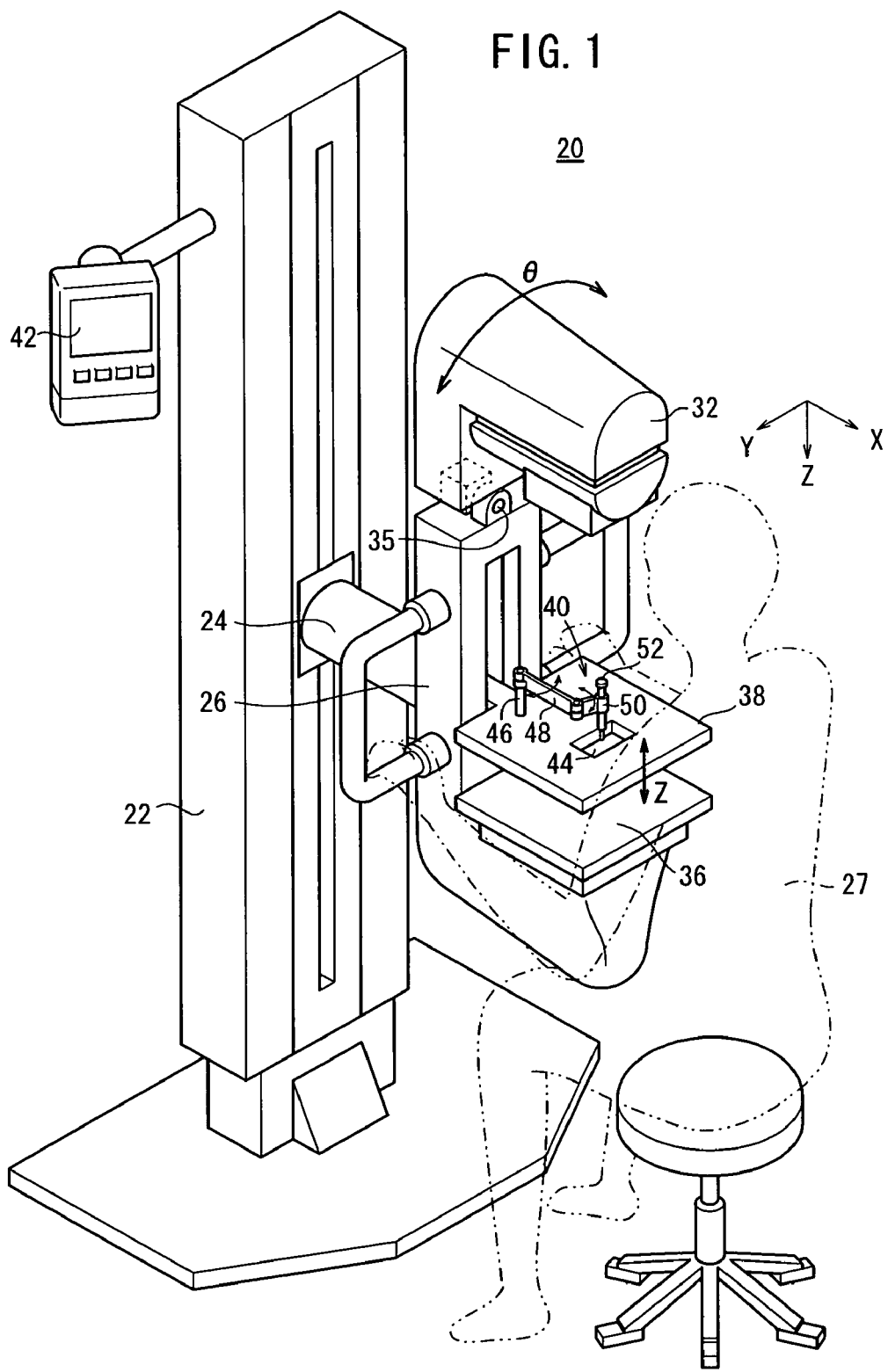
FIG. 1 is a perspective view of a mammographic apparatus, which incorporates therein a biopsy device according to an embodiment of the present invention.

Like or corresponding parts are denoted by like or corresponding reference characters throughout the views.

FIG. 1 shows in perspective a mammographic apparatus 20, which incorporates therein a biopsy device according to an embodiment of the present invention.

As shown in FIG. 1, the mammographic apparatus 20 includes an upstanding base 22, a vertical arm 26 fixed to a horizontal swing shaft 24 disposed substantially centrally on the base 22, a radiation source housing unit 32 housing therein a radiation source 30 (see FIG. 3) for applying radiation X to a breast 28 (a mass to be examined, see FIG. 2) of a subject 27, and which is fixed to an upper end of the arm 26, an image capturing base (support base) 36 mounted on a lower end of the arm 26 and housing therein a solid-state detector 34 (see FIGS. 2 and 3) for detecting radiation X that has passed through the breast 28, a compression plate 38 for compressing and holding the breast 28 against the image capturing base 36, and a biopsy hand assembly (biopsy needle moving mechanism) 40 for removing a tissue sample from a region 54 (see FIG. 2) to be biopsied (hereinafter referred to as a "biopsy region 54") of the breast 28. The biopsy hand assembly 40 is mounted on the compression plate 38.

To the base 22, there is connected a display control panel 42 for displaying image capturing information including an image capturing region, an image capturing direction, etc., of the subject 27, and ID information of the subject 27, etc., while also enabling setting of these items of information, if necessary.

When the arm 26, on which the radiation source housing unit 32 and the image capturing base 36 are secured, is angularly moved about the swing shaft 24, an image capturing direction with respect to the breast 28 of the subject 27 is adjusted. The radiation source housing unit 32 is operatively coupled to the arm 26 by a hinge 35, and can be turned independently of the image capturing base 36 about the hinge 35 in the directions indicated by the arrow θ. The compression plate 38, which is coupled to the arm 26, is disposed between the radiation source housing unit 32 and the image capturing base 36. The compression plate 38 is vertically displaceable along the arm 26 in the directions indicated by the arrow Z.

Figure 2:
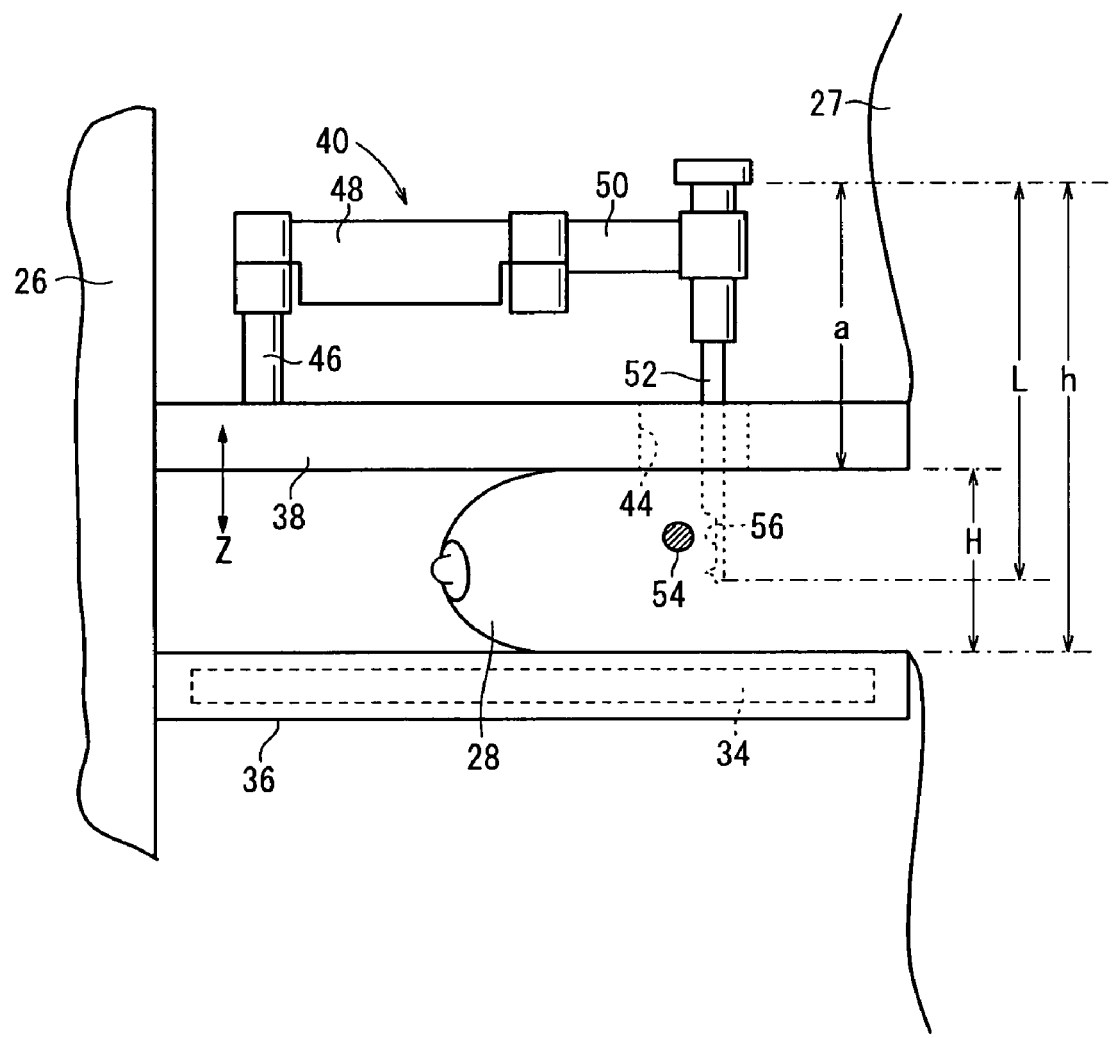
FIG. 2 is an enlarged fragmentary side elevational view of the mammographic apparatus, including a biopsy hand assembly of the biopsy device.

The compression plate 38 has an opening 44 defined therein for allowing the biopsy hand assembly 40 to remove a tissue sample from the biopsy region 54 of the breast 28. The biopsy hand assembly 40 comprises a post 46 fixedly mounted on the compression plate 38, a first arm 48 having one end thereof pivotally supported on the post 46 so that the first arm 48 is angularly movable about the post 46 along the surface of the compression plate 38, and a second arm 50 having one end thereof pivotally supported on the other end of the first arm 48 so that the second arm 50 is angularly movable about the other end of the first arm 48 along the surface of the compression plate 38. A biopsy needle 52 is mounted on the other end of the second arm 50 for movement in the directions indicated by the arrow Z, which are perpendicular to the compression plate 38. As shown in FIG. 2, the biopsy needle 52 has a sampler 56 (see FIG. 2) disposed proximate the lower end thereof for sampling under suction a tissue from the biopsy region 54 of the breast 28. The sampler 56 of the biopsy needle 52 can be moved in the vicinity of the biopsy region 54 when the first arm 48 and the second arm 50 of the biopsy hand assembly 40 are moved in an XY plane parallel to the surface of the compression plate 38, and the biopsy needle 52 is moved in the directions indicated by the arrow Z.

Figure 3:
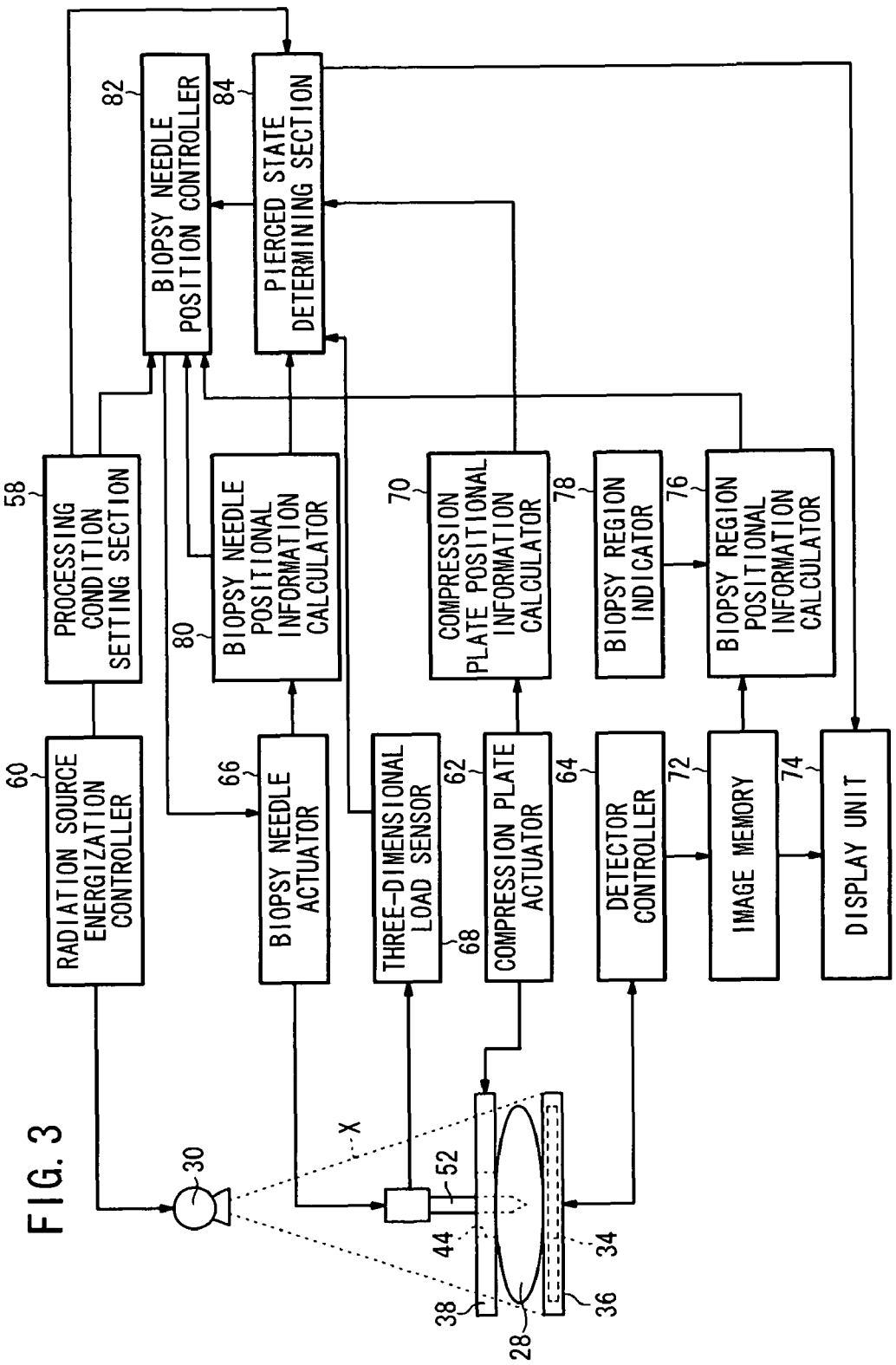
FIG. 3 is a block diagram of a control circuit for the mammographic apparatus.

FIG. 3 shows in block form a control circuit of the mammographic apparatus 20.

As shown in FIG. 3, the control circuit of the mammographic apparatus 20 includes a processing condition setting section (movement limiting quantity setting section) 58 for setting processing conditions including subject information such as the age, gender, body type, subject identification number, etc., of the subject 27, image capturing conditions for capturing radiation image information, a method for capturing the radiation image information, a movement limiting quantity applied to limit the distance that the biopsy hand assembly 40 moves, the length of the biopsy needle 52, etc., a radiation source energization controller 60 for energizing the radiation source 30 according to preset image capturing conditions including a tube current and a tube voltage of the radiation source 30, the type of target and filter that are set in the radiation source 30, an irradiation dose and an irradiation time of the radiation X, etc., a compression plate actuator 62 for moving the compression plate 38 in the directions indicated by the arrow Z (see FIG. 2), a detector controller 64 for controlling the solid-state detector 34 which detects radiation X that has been transmitted through the breast 28, a biopsy needle actuator 66 for causing the biopsy hand assembly 40 to move the biopsy needle 52 to a given position, and a three-dimensional load sensor (load detector) 68 for detecting loads that the biopsy needle 52 receives from the breast 28 in X, Y and Z directions, during times when the biopsy needle 52 is being inserted into the breast 28.

Positional information of the compression plate 38, when moved by the compression plate actuator 62 with respect to the image capturing base 36, is calculated by a compression plate positional information calculator 70. The detector controller 64 controls the solid-state detector 34 in order to acquire radiation image information of the breast 28, and stores the acquired radiation image information in an image memory 72. The radiation image information stored in the image memory 72 is displayed on a display unit (warning unit) 74, and also is supplied to a biopsy region positional information calculator 76. Positional information of the biopsy region 54, which is indicated by a biopsy region indicator 78, is calculated by the biopsy region positional information calculator 76. Positional information of the tip end of the biopsy needle 52, which is moved by the biopsy needle actuator 66, is calculated by a biopsy needle positional information calculator (positional information acquiring section) 80.

Positional information of the biopsy region 54, which is calculated by the biopsy region positional information calculator 76, is supplied to a biopsy needle position controller (movement limiter) 82. According to the positional information from the biopsy region 54, the biopsy needle position controller 82 controls the biopsy needle actuator 66 so as to move the biopsy needle 52 in the vicinity of the biopsy region 54. Positional information of the compression plate 38, which is calculated by the compression plate positional information calculator 70, and positional information of the tip end of the biopsy needle 52, which is calculated by the biopsy needle positional information calculator 80, are supplied to a pierced state determining section 84, which determines whether the biopsy needle 52 has pierced the breast 28. The pierced state determining section 84 can determine a pierced state that indicates how the breast 28 has been pierced by the biopsy needle 52, and a moved state that indicates how the biopsy needle 52 is moved, based on loads imposed on the biopsy needle 52, which are detected by the three-dimensional load sensor 68. When the pierced state determining section 84 judges that the biopsy needle 52 has pierced the breast 28, the biopsy needle position controller 82 controls the biopsy needle actuator 66 in order to limit movement of the biopsy needle 52. The distance by which the biopsy needle 52 is limited in movement can be set by the processing condition setting section 58.

Figure 4:
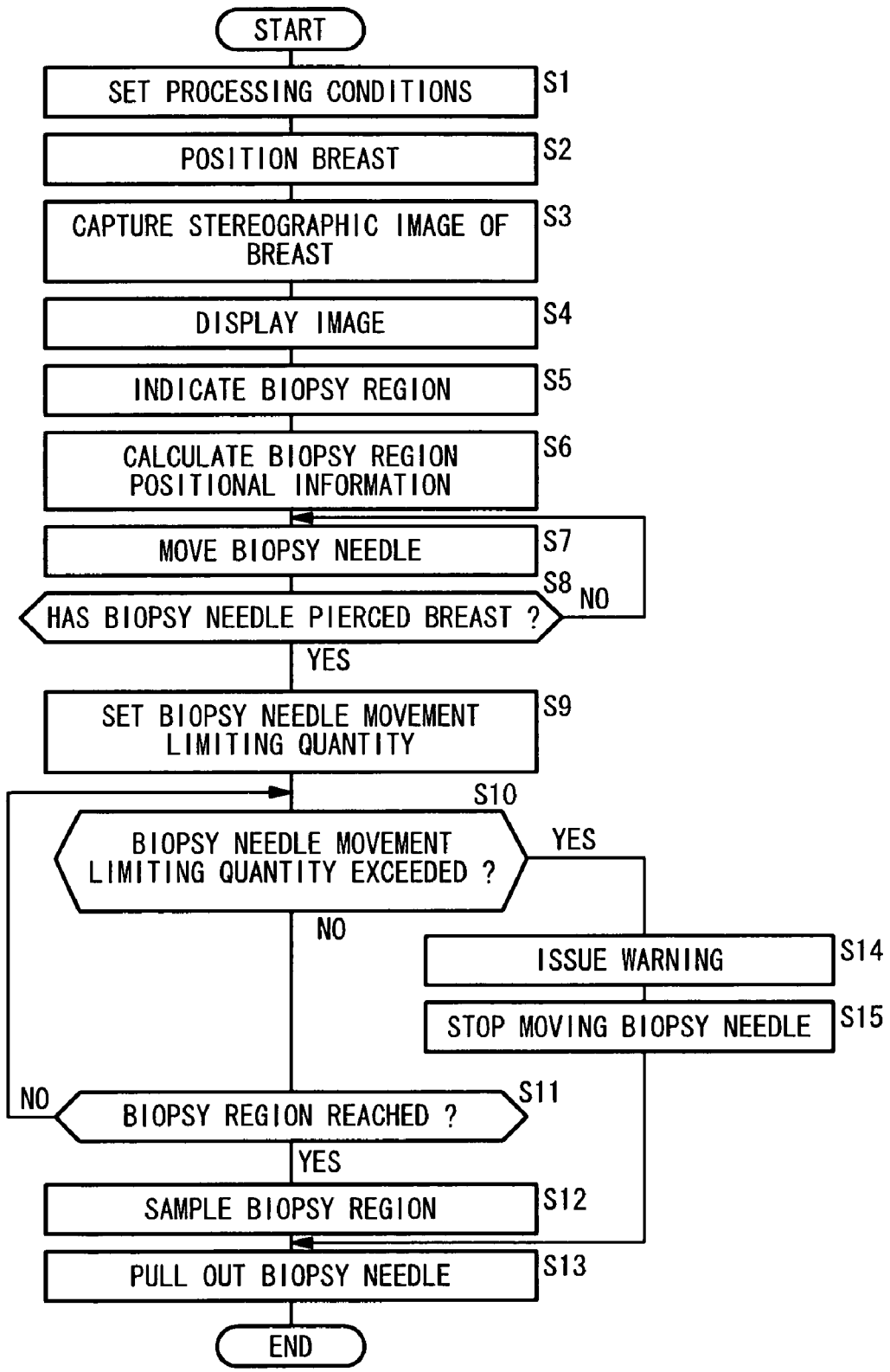
FIG. 4 is a flowchart of an operation sequence of the mammographic apparatus.

The mammographic apparatus 20 according to the present embodiment is basically constructed as described above. An operation sequence of the mammographic apparatus 20 will be described below, with reference to the flowchart shown in FIG. 4.

First, processing conditions, including subject information such as the age, gender, body type, subject identification number, etc., of the subject 27, image capturing conditions for capturing radiation image information, a method for capturing the radiation image information, a movement limiting quantity that limits the distance by which the biopsy hand assembly 40 is moved, the length of the biopsy needle 52, etc., are set by the processing condition setting section 58 (step S1). These processing conditions are displayed on the display control panel 42 of the mammographic apparatus 20 for confirmation. Among such set processing conditions, the image capturing conditions, including a tube current and a tube voltage of the radiation source 30, an irradiation dose, and an irradiation time of the radiation X, etc., are set in the radiation source energization controller 60. The movement limiting quantity, which limits the distance by which the biopsy hand assembly 40 is moved, is set in the biopsy needle position controller 82. Information concerning the length of the biopsy needle 52 is set in the pierced state determining section 84.

Then, a technician who is in charge of operating the mammographic apparatus 20 positions the breast 28 of the subject 27, according to the indicated capturing method for the radiation image information (step S2). More specifically, the technician places the breast 28 in a predetermined position on the image capturing base 36, and then energizes the compression plate actuator 62 so as to move the compression plate 38 toward the image capturing base 36, thereby compressing and positioning the breast 28 against the image capturing base 36.

Figure 5:
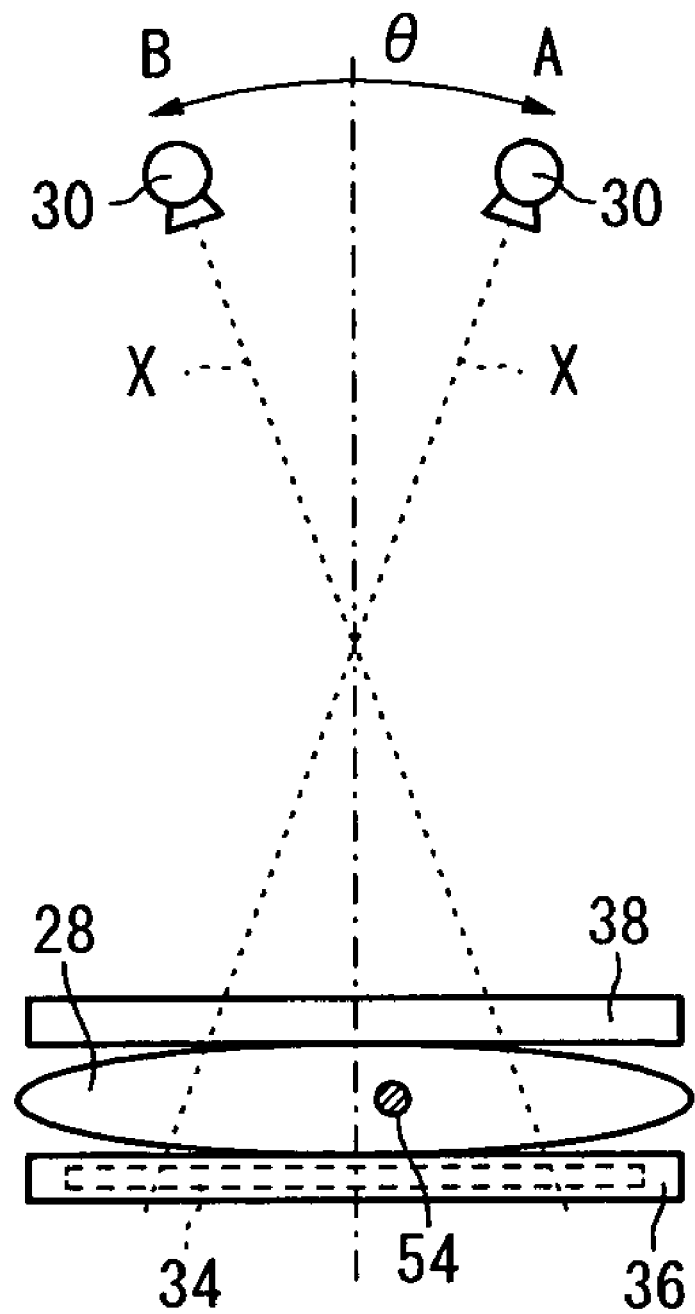
FIG. 5 is a schematic view that illustrates a stereographic imaging process carried out by the mammographic apparatus.

After the breast 28 has been positioned, the radiation source 30 is energized in order to capture a stereographic image of the breast 28 (step S3). More specifically, the radiation source housing unit 32 is turned about the hinge 35 (see FIG. 1), so as to place the radiation source 30 successively in the position A, and then in the position B (see FIG. 5). When the radiation source 30 is placed respectively in positions A and B, radiation images of the breast 28 are captured, thereby acquiring radiation image information of the breast 28 in positions A and B. In greater detail, the radiation source 30 is placed successively in position A and then in position B, and when the radiation source 30 is placed in positions A and B, the radiation source 30 emits radiation X, which passes through the breast 28 and is applied to the solid-state detector 34 in the image capturing base 36. The solid-state detector 34 detects radiation image information of the breast 28, based on the radiation X emitted from the radiation source 30, which has been placed in positions A and B. The detector controller 64 controls the solid-state detector 34 in order to acquire radiation image information of the breast 28 at positions A and B, and stores the acquired two items of radiation image information in the image memory 72. Thereafter, the detector controller 64 generates a stereographic image from the stored two items of radiation image information, and displays the generated stereographic image on the display unit 74 (step S4).

The technician uses the biopsy region indicator 78 in order to indicate a biopsy region 54 from the stereographic image displayed on the display unit 74 (step S5). The biopsy region indicator 78 may comprise a mouse or a touch panel.

Based on the biopsy region 54 indicated by the technician, and from the two items of radiation image information stored in the image memory 72, the biopsy region positional information calculator 76 calculates positional information concerning the biopsy region 54 (step S6). Such positional information comprises three-dimensional positional information of the biopsy region 54. The biopsy region positional information calculator 76 supplies the calculated positional information concerning the biopsy region 54 to the biopsy needle position controller 82.

Based on the positional information of the biopsy region 54, which is supplied from the biopsy region positional information calculator 76, the biopsy needle position controller 82 controls the biopsy needle actuator 66 in order to move the biopsy needle 52 to a corresponding position (step S7). Based on positional information in both X and Y directions of the biopsy region 54, the biopsy hand assembly 40 moves the first arm 48 and the second arm 50 in the XY plane, so as to position the biopsy needle 52 above the biopsy region 54. Then, the biopsy needle 52 moves in a downward direction, as indicated by the arrow Z, whereupon the biopsy needle 52 becomes inserted into the breast 28 through the opening 44 in the compression plate 38.

Positional information in the Z direction of the biopsy needle 52 is sequentially calculated by the biopsy needle positional information calculator 80, and is supplied to the pierced state determining section 84. The pierced state determining section 84 determines whether or not the biopsy needle 52 has pierced the breast 28, based on the positional information of the compression plate 38, which is calculated by the compression plate positional information calculator 70, the positional information in the Z direction of the biopsy needle 52, which is calculated by the biopsy needle positional information calculator 80, and information concerning the length of the biopsy needle 52, which is supplied from the processing condition setting section 58 (step S8).

As shown in FIG. 2, it is assumed that the length of the biopsy needle 52 is represented by L, the distance from the image capturing base 36 to the compression plate 38 is represented by H, the distance from the image capturing base 36 to the upper end of the biopsy needle 52 is represented by h, and the distance from the compression plate 38 to the upper end of the biopsy needle 52 is represented by a. In this case, the distance h is calculated as follows:

$$h = a + H$$

Further, if the following relationship is satisfied, it is judged that the biopsy needle 52 has pierced the breast 28.

$$(h - L) < H$$

The three-dimensional load sensor 68 is connected to the biopsy needle 52. The pierced state determining section 84 judges that the biopsy needle 52 has pierced the breast 28 when the load applied to the biopsy needle 52 in the Z direction, which is indicated by a detected load signal from the three-dimensional load sensor 68, is equal to or greater than a predetermined threshold value.

The pierced state determining section 84 determines a pierced state based on the length L of the biopsy needle 52 as well as the distances H and h. The pierced state determining section 84 also determines the pierced state based on the detected load signal from the three-dimensional load sensor 68. Therefore, the pierced state determining section 84 reliably determines whether the biopsy needle 52 has pierced the breast 28.

When the biopsy needle position controller 82 is supplied with a pierce signal from the pierced state determining section 84, which indicates that the biopsy needle 52 has pierced the breast 28, the biopsy needle position controller 82 sets a movement limiting quantity in the biopsy needle actuator 66 for limiting the distance that the biopsy needle 52 moves in the XY plane (step S9). The movement limiting quantity can be set by the processing condition setting section 58. At this time, the biopsy needle position controller 82 may set movement limiting quantities in respective X and Y directions in order to perform fine positional adjustments in the X and Y directions of the biopsy needle 52 with respect to the biopsy region 54 while the biopsy needle 52 is being inserted into the breast 28.

While the movement of the biopsy needle 52 in the XY plane is limited according to the set movement limiting quantities (step S10), the biopsy needle position controller 82 controls the biopsy needle actuator 66 so as to move the biopsy needle 52 downwardly in the Z direction, based on positional information in the Z direction of the biopsy needle 52 which is supplied from the biopsy region positional information calculator 76, and until the sampler 56 (see FIG. 2) of the biopsy needle 52 reaches a position near to the biopsy region 54 (step S11). Since movement of the biopsy needle 52 in the XY plane is limited at this time, the biopsy needle 52, which is inserted into the breast 28, cannot accidentally be moved in the X or Y direction, and hence the biopsy needle 52 is prevented from causing damage to the breast 28.

When the sampler 56 of the biopsy needle 52 reaches a position near to the biopsy region 54, the biopsy needle 52 begins to apply suction to the biopsy region 54 to sample the biopsy region 54 (step S12). Thereafter, the biopsy needle position controller 82 controls the biopsy needle actuator 66 so as to move the biopsy needle 52 upwardly in the Z direction, until the biopsy needle 52 is pulled out of the breast 28 (step S13), whereupon the tissue sampling process is finished.

If the distance that the biopsy needle 52, which is inserted into the breast 28, moves in the X or Y direction exceeds the movement limiting quantity (step S10), then the pierced state determining section 84 judges that the biopsy needle actuator 66 is malfunctioning, and issues a warning to the technician from the display unit 74 (step S14). The pierced state determining section 84 then causes the biopsy needle position controller 82 to control the biopsy needle actuator 66 to stop movement of the biopsy needle 52 (step S15), and then the biopsy needle actuator 66 pulls the biopsy needle 52 out of the breast 28 (step S13). In this manner, damage caused to the biopsy region 54 by the biopsy needle 52 can be minimized.

Rather than determining whether the distance that the biopsy needle 52 has moved exceeds the movement limiting quantities, the pierced state determining section 84 may determine whether or not the load in the X or Y direction, which is detected by the three-dimensional load sensor 68, is equal to or greater than a predetermined threshold value, whereupon the pierced state determining section 84 may issue a warning and stop movement of the biopsy needle 52 if the detected load is equal to or greater than the predetermined threshold value. In this case, damage caused to the biopsy region 54 by the biopsy needle 52 is minimized, not only when the biopsy needle 52 moves abnormally, but also when the subject 27 moves during periods when the biopsy needle 52 is being inserted into the breast 28.

Figure 6:
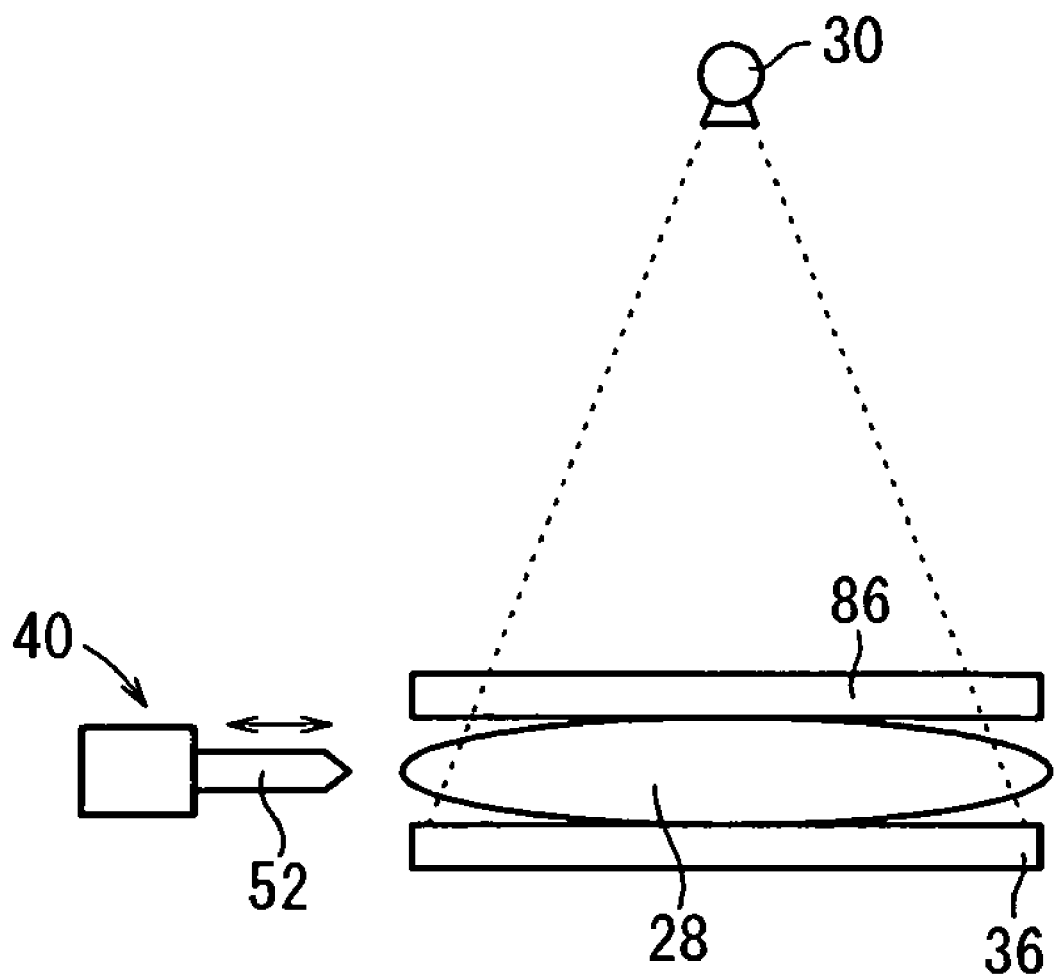
FIG. 6 is a schematic view of a mammographic apparatus, which incorporates therein a biopsy device according to another embodiment of the present invention.
Figure 7:
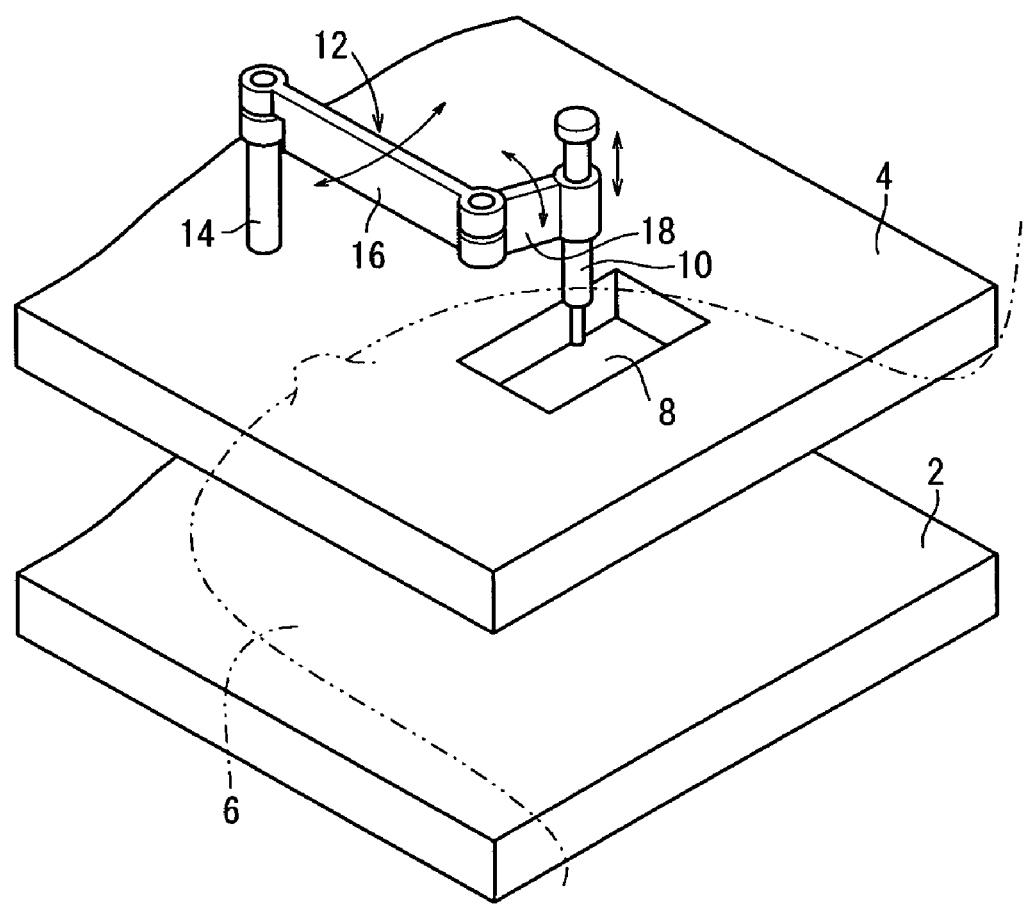
FIG. 7 is a fragmentary perspective view of a biopsy device according to a conventional technique.

FIG. 6 shows schematically a mammographic apparatus, which incorporates therein a biopsy device according to another embodiment of the present invention. With the biopsy device shown in FIG. 6, rather than going through the compression plate 86, the biopsy needle 52 is inserted into the breast 28, which is compressed between the image capturing base 36 and the compression plate 86, laterally from one side of the breast 28 between the image capturing base 36 and the compression plate 86. The other principles of the present invention, as described above, are applicable to the biopsy device shown in FIG. 6.

The principles of the present invention are not limited to biopsy devices that are incorporated in mammographic apparatus, but also may be applicable to other types of biopsy devices that are used for performing a biopsy.

Although certain preferred embodiments of the present invention have been shown and described in detail, it should be understood that various changes and modifications may be made to the embodiments without departing from the scope of the invention as set forth in the appended claims.

What is claimed is:

1. A biopsy device comprising:

a biopsy needle moving mechanism for moving a biopsy needle to be inserted into a biopsy region of a mass to be examined in a piercing direction along which the biopsy needle pierces the mass to be examined and in a direction perpendicular to the piercing direction;

a determining section for determining whether the biopsy needle has pierced the mass to be examined or not;

a biopsy needle actuator for causing the biopsy needle moving mechanism to move the biopsy needle to a given position;

a compression plate for compressing the mass to be examined, the compression plate having an opening defined therein through which the biopsy needle is movable; and a movement limiter comprising a biopsy needle position controller, which is disposed separately from the mass to be examined, for controlling the biopsy needle actuator, wherein the movement limiter controls the biopsy needle actuator such that movement of the biopsy needle within a plane perpendicular to the piercing direction along which the biopsy needle pierces the mass to be examined is limited, thereby to prevent unintentional movement of the biopsy needle within the plane perpendicular to the piercing direction, on condition that the determining section judges that the biopsy needle has pierced the mass to be examined, and wherein the movement limiter controls the biopsy needle actuator such that the movement of the biopsy needle within the plane perpendicular to the piercing direction is limited to within an opening range of the opening.

2. A biopsy device according to claim 1, further comprising:

a movement limiting quantity setting section for setting a movement limiting quantity by which movement of the biopsy needle is limited by the movement limiter.

3. A biopsy device according to claim 1, further comprising:

a positional information acquiring section for acquiring positional information of the biopsy needle with respect to the piercing direction, wherein the determining section determines whether the biopsy needle has pierced the mass to be examined or not, based on the positional information.

4. A biopsy device according to claim 1, further comprising:

a load detector for detecting a load imposed on the biopsy needle when the biopsy needle moves with respect to the piercing direction, wherein the determining section determines that the biopsy needle has pierced the mass to be examined, when the load detected by the load detector is equal to or greater than a predetermined value.

5. A biopsy device according to claim 1, further comprising:

a load detector for detecting a load imposed on the biopsy needle when the biopsy needle moves in the plane perpendicular to the piercing direction, wherein the movement limiter controls the biopsy needle actuator such that movement of the biopsy needle is stopped when the load detected by the load detector is equal to or greater than a predetermined value.

6. A biopsy device according to claim 5,
wherein the biopsy needle actuator causes the biopsy needle moving mechanism to pull the biopsy needle out of the mass to be examined, after the biopsy needle has been stopped by the movement limiter.

7. A biopsy device according to claim 1, further comprising:
a load detector for detecting a load imposed on the biopsy needle when the biopsy needle moves in the plane perpendicular to the piercing direction; and
a warning unit for issuing a warning when the load detected by the load detector is equal to or greater than a predetermined value.

8. A biopsy device according to claim 1, further comprising:
a support base for supporting the mass to be examined,
wherein the biopsy needle moving mechanism moves the biopsy needle in a plane along the compression plate as well as in directions perpendicular to the compression plate.

9. A biopsy device according to claim 1, further comprising:
a support base for supporting the mass to be examined,
wherein the biopsy needle moving mechanism moves the biopsy needle laterally between the support base and the compression plate.

* * * * *